(12) United States Patent
Hartmann et al.

(10) Patent No.: US 6,345,191 B1
(45) Date of Patent: Feb. 5, 2002

(54) SYSTEM FOR QUANTITATIVE DETERMINATION OF THE LOCAL DISTRIBUTION OF A QUANTITY TO BE MEASURED

(75) Inventors: Paul Hartmann, Weiz; Werner Ziegler, Graz, both of (AT)

(73) Assignee: F. Hoffman-La Roche AG, Basel (CH)

( * ) Notice: Subject to any disclaimer, the term of this patent is extended or adjusted under 35 U.S.C. 154(b) by 0 days.

(21) Appl. No.: 09/536,726

(22) Filed: Mar. 28, 2000

(30) Foreign Application Priority Data

Mar. 29, 1999 (EP) .............................. 99890109

(51) Int. Cl.[7] .......................... A61B 5/00; G01N 21/29; G01N 21/64; G01N 31/12; G01N 21/76
(52) U.S. Cl. ...................... 600/310; 600/317; 436/172; 422/80; 422/82.05; 422/82.08
(58) Field of Search ................................ 600/310, 317, 600/309, 311, 312, 322, 323, 324, 326, 329, 336, 344, 345, 348, 353, 354, 355, 357, 361, 363, 364, 407, 476; 436/127, 164, 165, 172; 422/79, 80, 82.08, 82.05; 356/39

(56) References Cited

U.S. PATENT DOCUMENTS

| | | | |
|---|---|---|---|
| 4,041,932 A | | 8/1977 | Fostick |
| 4,259,963 A | | 4/1981 | Huch |
| 5,370,114 A | * | 12/1994 | Wong et al. ................. 600/322 |
| 5,485,530 A | | 1/1996 | Lakowicz et al. |
| 5,593,899 A | | 1/1997 | Wilson et al. |
| 5,643,681 A | | 7/1997 | Voorhees et al. |
| 5,851,181 A | * | 12/1998 | Talmor ........................ 600/407 |
| 6,147,761 A | * | 11/2000 | Walowit et al. ............. 356/425 |

FOREIGN PATENT DOCUMENTS

| | | |
|---|---|---|
| DE | 3900191 | 7/1990 |
| EP | 0516610 | 6/1995 |

OTHER PUBLICATIONS

Hartmann et al., "Fluorescence Lifetime Imaging of the Skin $PO_2$: Instrumentation and Results" in ISOTT 1996.

Holst et al., "A Modular Luminescence Lifetime Imaging System for Mapping Oxygen Distribution in Biological Samples" in Sensors and Actuators B 51 (1998) pp. 63–170.

* cited by examiner

Primary Examiner—Robert L. Nasser
Assistant Examiner—Navin Natnithithadha
(74) Attorney, Agent, or Firm—Dykema Gossett, PLLC

(57) ABSTRACT

A system for quantitative determination of the local distribution of a quantity to be measured, comprising a planar sensor film, which is applied to a measuring surface, such as the surface of a body organ, a skin area or a cell culture, and whose diffusion properties regarding a parameter to be determined are known. The sensor film contains a luminescent indicator responding to the parameter to be determined with a change of at least one optical property. The system further comprises an excitation and detection unit including means for supplying excitation radiation of at least one wavelength, an imaging detection means, preferably a CCD camera, and an evaluation unit processing the image information obtained from the excitation and detection unit. Further provided is an applicator tube to be placed on the measuring surface, whose rim facing the measuring surface is in elastic contact with the sensor film and is impervious to external radiation interfering with the detection means. At the other end facing away from the measuring surface, which may be covered with a cap, a coupling means is provided for attachment of the excitation and detection unit.

23 Claims, 3 Drawing Sheets

SYSTEM FOR QUANTITATIVE DETERMINATION OF THE LOCAL DISTRIBUTION OF A QUANTITY TO BE MEASURED

BACKGROUND OF THE INVENTION

The invention relates to a system for quantitative determination of the areal distribution of a quantity to be measured, including a planar sensor film, which is applied to a possibly curved measuring surface, such as the surface of a body organ, a region of the skin or a cell culture, and whose diffusion properties regarding a parameter to be determined are known, said sensor film containing a luminescent indicator responding to the parameter to be determined with a change of at least one optical property, and comprising an excitation and detection unit including a means for supplying excitation radiation of at least one wavelength and an imaging detection means, preferably a CCD camera, and an evaluation unit processing the image information obtained from the excitation and detection unit.

DESCRIPTION OF THE PRIOR ART

In medical diagnosis and in the monitoring and control of medical treatment it may be most desirable to determine the areal distribution of the concentration of a measurement variable on the surface of a body organ, such as the skin, or the distribution of the flow rate of a given substance through a boundary surface, such as a surface of a body organ, a region of the skin, or a cell culture in a laboratory set-up.

In this context a schematical configuration has become known from EP 0 516 610 B1, by means of which readings for the material flux, such as oxygen flux, through an interface, such as a skin surface, may be taken. The sensing layer of the measuring device, which is assigned to the boundary face or measuring surface, will exert a known or predefined, finite resistance to the material flux to be determined, at least one optical indicator being provided in the sensing layer for determining the material concentration on one side of the sensing layer. The measured or known concentration value on the other side of the sensing layer, or the difference relative to the first concentration value, is used to determine the material flux through the boundary face. In a variant of the invention the surface of the sensing layer is scanned by a plurality of detectors or by means of an imaging system (CCD).

In U.S. Pat. No. 5,593,899 an apparatus and method for measuring tissue oxygenation are disclosed, using the oxygen dependent quenching of a fluorescent indicator. To measure oxygen supply, a luminescent layer, which is part of a skin cream, is applied to a particular surface region of the skin, and is covered with an oxygen-impermeable film. The optical device enclosed in a plastic housing is provided with a plastic or glass cover which is directly placed over the $O_2$-impermeable film. Further included are an interference filter and a photodiode. Via optical fiberguides the luminescent layer is exposed to excitation radiation from a modulated radiation source. The plastic housing further includes heating elements, which are connected to a thermoregulation circuit and heat up the measuring region to a temperature of 39° to 42° C. The arrangement described in this document is suitable only for integrated measurements over the entire measuring region covered by the optical device. It does not yield accurate information on boundaries between regions with satisfactory oxygen supply and those with oxygen deficiency.

Theoretical considerations on the local distribution of oxygen flux or subcutaneous oxygen concentration and a proposal concerning an imaging technique are disclosed in "Fluorescence Lifetime Imaging of the Skin $PO_2$: Instrumentation and Results" in *Advances in Experimental Medicine and Biology*, Vol. 428, 605–611 (1997), Plenum Press, N.Y. In this article a sensor membrane measuring transcutaneous oxygen concentration is described, which consists of an optical isolating layer next to the skin, a sensing layer containing a luminescent indicator with $O_2$-sensitive decay time, and an oxygen-impermeable supporting foil. Another membrane measuring oxygen flux, which is also described in this paper, differs from the former by a diffusion barrier with known oxygen permeability, which is used instead of the $O_2$-impermeable layer. For the measuring process the sensor membrane is applied to the measuring surface, for example, a region of skin. A modulation technique is employed for measuring, where the LEDs emitting excitation radiation in the direction of the sensor membrane are driven by a square-wave generator. The phase-shifted light radiation emitted by the sensor membrane is detected by a CCD camera with modulated amplification and transmitted pixel by pixel to a computing unit for image-processing. Images of the oxygen distribution measured in a polymer layer as compared to the inhomogeneous oxygen distribution over a region of the skin are part of the documentation.

Other imaging methods using phase fluorimetry are disclosed in U.S. Pat. No. 5,485,530.

Finally, the paper "A modular luminescence lifetime imaging system for mapping oxygen distribution in biological samples" published in *Sensors and Actuators* B 51 (1998) 163–170, is concerned with an imaging method measuring two-dimensional oxygen distributions with planar optodes. The experimental set-up includes a test chamber with several perfusion channels, through which water with different oxygen concentrations is guided. In the direction of the optical system the channels are closed with a planar optode pressed against the test chamber. For excitation of the planar optode a fiber-optical ring light source is employed, radiation detection is effected by means of a CCD camera.

SUMMARY OF THE INVENTION

It is an object of this invention to further develop the above system so as to obtain reproducible measurement results of the areal or local distribution of the concentration of a measurement variable over a possibly curved surface, or the areal distribution of the material flux through a possibly curved surface, and to display the obtained results with the use of an imaging method.

According to the invention this object is achieved by providing the apparatus with an applicator tube to be placed over the measuring surface, whose rim facing the measuring surface is in elastic contact with the sensor film and is impervious to external radiation interfering with the detection means.

Following is a more detailed discussion of the present invention which is exemplified by measurements of the areal distribution of the transcutaneous oxygen concentration and the areal distribution of the oxygen flux through the skin, this does not imply that the invention is restricted to this specific purpose, the advantages obtained by this procedure will be fully applicable in the case of other medical or biological quantities and parameters. With a suitably chosen luminescent indicator it will be possible, for example, to measure the subcutaneous $CO_2$ concentration or distribution of the $CO_2$ flux through the skin. The system of the invention could also be employed for determining the areal distribution of the concentration or flux of ions, if the sensor film which is applied to the measuring surface, includes a luminescent indicator responding to the ion in question.

Use of the applicator tube to be placed on the measuring surface will result in an unambiguously defined optical configuration yielding reproducible measurement results. With its elastic rim that is in elastic contact with the sensor film, and its constant distance to the measuring surface given by the length of the tube, the applicator tube serves to protect the sensitive detection unit from straylight or undesirable background radiation. This is also true for uneven surfaces onto which the elastic rim fits closely.

The system is particularly suitable for use with curved measuring surfaces, for example, for measuring subcutaneous oxygen concentrations in a patient's limbs, where the detection means preferably includes a unit for determining the local fluorescence decay time or a derived quantity. To obtain an imaging technique that is independent of inhomogeneities of the distribution of the luminescent indicator in the sensor film, and of inhomogeneous optical conditions, the invention preferably relies on decay time measurement. A special CCD camera is operated in such a way that the information in each pixel can be correlated with the decay time prevailing at the measuring site corresponding to the pixel. The special advantage of measuring a parameter that is exclusively defined by the decay time of the indicator, is that the measurement will become independent of the local illuminance at the sensor film. As a consequence, it will be possible to illuminate even curved surfaces by means of a simple configuration of the excitation light source, without having to provide means for homogeneous illumination, as long as sufficient luminescence radiation is generated for decay time measurement in each measuring point. Since decay time measurement, as opposed to intensity measurement, is not subject to any dependence on the square of the distance of the measured object, and since different propagating times of the light due to different distances of the measured object are negligible from the point of measuring accuracy at the modulation frequencies used in this context, decay time measurement is most suitable for measurements involving the arms or legs, or other curved areas of a patient's skin.

It is provided in a preferred variant of the invention that the applicator tube be provided at its sealable end facing away from the measuring surface with a coupling means for attaching the excitation and detection unit.

According to the invention the applicator tube may be covered at the end facing away from the measuring surface by a cover plate that is transparent to the excitation and measurement radiation, i.e., a glass plate preferably, or by a removeable cap. This is particularly useful if the sensor film or the measuring region must be thermoregulated prior to measuring until a constant temperature is reached, which process may take several minutes.

In a first variant of the invention the applicator tube may be have inlet and outlet openings through which a heat transfer medium, preferably hot air, is introduced and carried off for thermoregulation of the sensor film. By heating the skin area to temperatures >33° C., and preferably 37° C., the activity of the skin is increased. This will reduce the waiting time required until the oxygen concentration at the interface between skin and sensor film has reached its equilibrium with the $O_2$ concentration in subcutaneous layers of tissue. It is only after this delay that the sensor will measure the oxygen concentration corresponding to the subcutaneous oxygen partial pressure. Introducing thermoregulation will reduce the preparation time for the actual measurement, and thus will relieve both patient and clinical staff. Due to the use of the applicator tube described by the invention the patient is not connected to the excitation and detection unit during the adjustment or waiting period, and is thus capable of moving more or less freely. The excitation and detection unit of the system will have to be attached to the coupling means of the applicator tube only just before measurement.

According to the invention the applicator tube could also be provided with a radiation- or heating-element for thermoregulation of the sensor film, such as an infrared light source or an electric heater coil.

As regards the applicator tube the planar sensor film is not subject to any restrictions, and could be provided as a sensor paste applied to the measuring surface, or a sensing foil, or a spray layer.

One and the same type of system as described by the invention may be employed for measuring both concentration or partial pressure and flux, the only distinction being the use of different sensor films. Concentration or partial pressure are measured by means of a sensor film whose side facing away from the measuring surface exhibits a barrier layer that is impermeable to the parameter to be determined. Flux measurements, on the other hand, employ a sensor film which may include additional supporting and filling layers consisting of materials which exhibit a known, finite resistance to the passage of the parameter to be determined.

In a preferred variant of the invention the proposal is put forward that a flexible layer be provided between the sensor film and the measuring surface to bridge the gap between sensor film and measuring surface, i.e., preferably an adhesive layer which is permeable to the parameter to be determined. This will permit the efficient reduction of transverse diffusions of the measured parameter as compared to the rapid diffusion in an air gap, and an improvement of the areal resolution of the measurements. A further advantage is obtained by providing that the flexible layer between sensor film and measuring surface be impervious to radiation interfering with the detection unit (such as the intrinsic fluorescence of the skin).

To permit proper alignment of the excitation and detection unit, the latter is designed such that it can be attached to the coupling means of the applicator tube so as to be rotatable about its optical axis.

If the apparatus is to be fastened to a patient's arms or legs, the applicator tube can be fixed at the measurement site by means of a cuff.

For measurement of the oxygen concentration or oxygen flux a luminescent indicator should be immobilized in the sensor film, or the sensor film should be coated with a luminescent indicator whose local luminescence quenching is a unique function of the local oxygen concentration.

DETAILED DESCRIPTION OF THE PREFERRED EMBODIMENT

Figure 1:
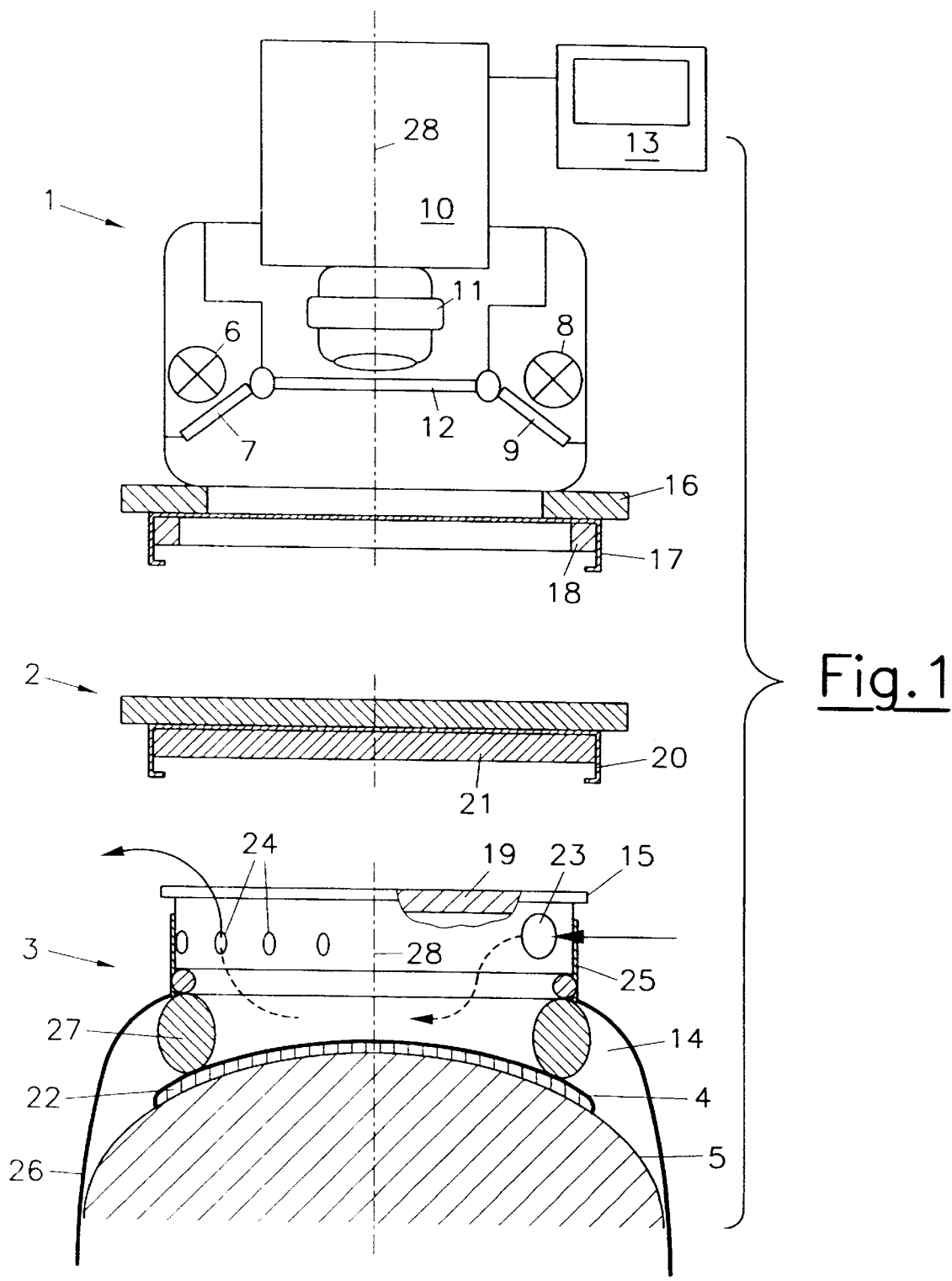
FIG. 1 is a partial axial section of a system in accordance with the present invention.

The variant of a system for quantitative determination of the areal distribution of a quantity to be measured as proposed by the invention and as shown in FIG. 1 is essentially configured as a three-part unit comprising an excitation and detection unit 1, a removable cap 2, and an applicator tube 3. The system further includes a planar sensor film 4, which is designed for application to a curved measuring surface 5, such as a region of the skin on the arm of a patient. The sensor film 4 is provided with a luminescent indicator responding to the parameter to be determined by a change of at least one optical property. The excitation and detection unit 1 includes means providing excitation radiation of one or more wavelengths, for example, a light source 6 and an excitation filter 7 supplying radiation of the wavelength $\lambda_1$, and a light source 8 and an excitation filter 9 supplying radiation of the wavelength $\lambda_2$. The imaging detection means 10 comprises a CCD camera with an imaging lens 11, for instance, as well as an emission filter 12. The detection means is connected to an evaluation unit 13 (shown here only schematically) processing the image information obtained by the excitation and detection unit 1.

The evaluation unit 13 includes means for image processing and filing, information processing (e.g., display as false color images, histograms, etc.).

The applicator tube 3 to be placed on the measuring surface 5 has a rim 14 facing the measuring surface, which is in elastic contact with the sensor film 4 and eliminates undesirable radiation noise. The end of the applicator tube 3 facing away from the measuring surface 5 is provided with a coupling means 15 for the excitation and detection unit 1.

The removeable cap 2 is useful for purposes in which the sensor film 4, or rather, the skin region covered by it, must be thermoregulated before the beginning of the measuring process. If no thermoregulation is required the cap 2 may be omitted and the excitation and detection unit 1 may be directly attached to the applicator tube 3, the fastener 17 sitting on a supporting ring 16 (a bayonet lock or quarter-turn fastener, for instance) locking onto the coupling means 15 of the applicator tube 3. A sealing ring 18 beneath the supporting ring 16 serves for light-proof coupling of the detection unit.

According to a variant of the invention the end of the applicator tube 3 facing away from the measuring surface 5 may be covered by a cover 19 that is transparent to the excitation and measurement radiation, for example, a glass cover, thus permitting thermoregulation of the space enclosed by the applicator tube 3 and eliminating the need for the removeable cap 2. The removeable cap 2 has the same fastener 20 as the excitation and detection unit 1, and may be provided with a sealing or insulating layer 21 on its inside.

Between sensor film 4 and measuring surface 5 a flexible layer 22 bridging the gap is provided, which is permeable to the parameter to be determined. Since both sensor film 4 and flexible layer 22 can be made very thin, the local oxygen concentration in the sensor film may be determined with high areal resolution, limits to local differentiation being essentially set by the diffusion properties of the skin rather than the measuring equipment.

To optimize measuring accuracy and reproducibility the applicator tube 3 includes means for thermoregulation of the sensor film 4 and the skin region underneath. Such means may comprise inlet and outlet openings 23 and 24, respectively, for a heat transfer medium, preferably hot air.

For attachment to the arms or legs of a patient, the applicator tube 3 may preferably be provided with a back-up ring 25, which is fastened to the limb by means of a cuff 26. The elastic rim of the applicator tube adjacent to the measuring surface 5 or sensor film 4 and serving as a supporting ring 27 may be made of flexible material, foamed plastic, microcellular rubber, gas-filled tubing, or similar. The supporting ring 27 will limit the detection field of the detection means 10 (see FIG. 3). The diameter of this ring is smaller than the sensor film applied, as the peripheral regions of the sensor film cannot be fully utilized for measuring purposes, and as the ring may be used to keep the sensor film in place. The flexible supporting ring 27 also serves as a seal when hot air heating is used.

The applicator tube 3 together with its back-up ring 25 and the fastening cuff 26 constitutes the part of the measuring system that is immovable relative to the sensor film 4. It serves as a support for the objetive tube of the excitation and detection unit which is attached to the coupling means 15 of the applicator tube 3 so as to be rotatable about its optical axis 28. This will permit the CCD camera to be brought into the position desired.

Figure 2:
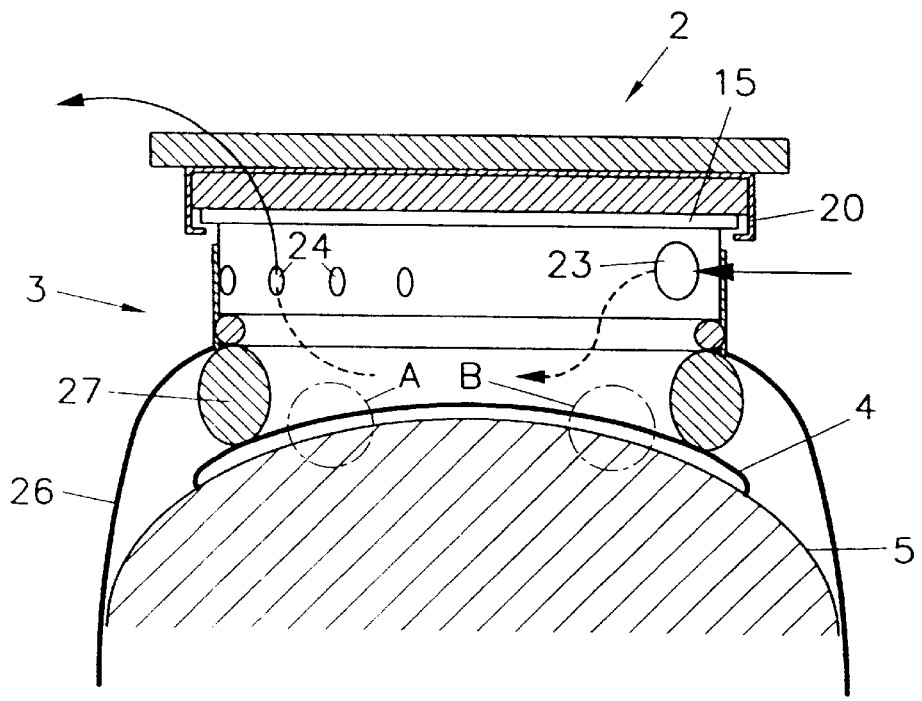
FIG. 2 shows the applicator tube in accordance with the present invention, including the removeable cap.

In FIG. 2 the applicator tube 3 is covered with the removeable cap 2 during thermoregulation. The locking elements 20 lock with the coupling means 15 of the applicator tube 3. Through the inlet opening 23 the heat transfer medium, i.e., hot air, for example, will enter the tube, leaving it through outlet openings 24 which are arranged such that a homogeneous flow through the volume will be ensured. The outlet openings 24 must be made impervious to light, using filter elements, for instance. Further provided is a temperature sensor (not shown here) forming a closed control loop with an external heater-blower unit. In this way the sensor film and skin region lying underneath may be adjusted to a stable temperature of 33° C. to 37° C. Another temperature sensor connected to the evaluation unit may be provided for monitoring the temperature in the tube.

As already shown as a variant in FIG. 1, the applicator tube 3 may be covered by a transparent glass plate 19. In this variant the removeable cap 2 is omitted. The use of a glass plate may lead to undesirable reflections of the excitation or fluorescence light, however. Both designs, i.e., the one with the removeable cap 2 and that with a transparent plate 19, have the advantage that the excitation and detection unit 1 may be decoupled during the warm-up phase, which will relieve the patient from the weight of the camera. Moreover, the excitation and detection unit 1 may be used for other patients during the warm-up phase.

Figure 2A:
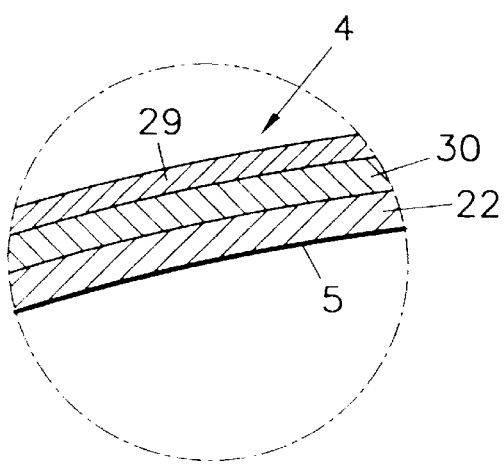
FIGS. 2a and 2b are sectional representations of two variants of the sensor film used with the system in accordance with the present invention.
Figure 2B:
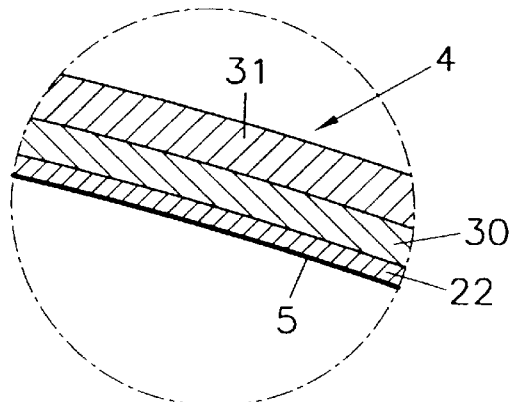

FIGS. 2a and 2b show enlarged details of Variants A and B of the sensor film 4. In both cases a flexible layer 22 is provided directly on the measuring surface 5, i.e., the skin, for example, which layer may be configured as part of the sensor film or as an adhesive layer that is directly applied to the skin in order to bridge the gap between measuring surface and sensor film. The layer is preferably configured as optical isolation layer. It must be permeable to the parameter to be determined, however. For measuring the transcutaneous oxygen concentration the sensor film shown in FIG. 2a is provided with a barrier layer 29 on the side facing away from the measuring surface 5, which barrier layer 29 is impermeable to the measured parameter. The indicator layer bears reference number 30.

For measuring the oxygen flux the sensor film 4 in FIG. 2b is provided with a supporting layer 31 in addition to the indicator layer 30. The supporting layer 31 consists of material exhibiting a known, finite resistance to the passage of the measured parameter. It would also be possible to produce the indicator layer 30 using matrix material or including filler layers presenting a diffusion barrier to the parameter to be determined, such as oxygen, for example.

Figure 3:
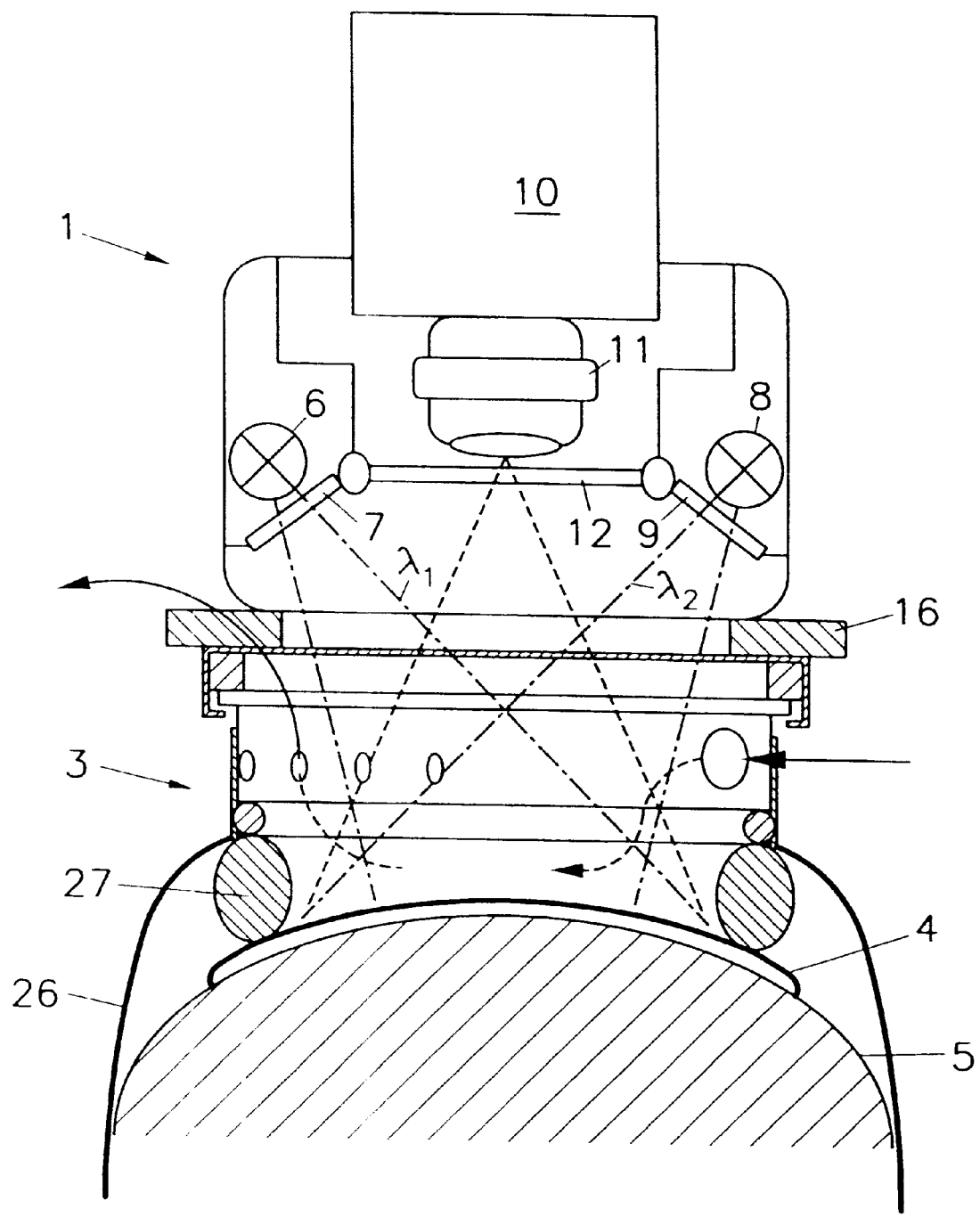
FIG. 3 shows the system in accordance with the present invention during the measuring phase.

In FIG. 3 the system of the invention is shown during the measuring phase. For this purpose the excitation and detection unit 1 is coupled to the applicator tube 3. Unit 1 includes one or several light sources 6, 8, which are arranged so as to provide a most homogeneous illumination of the sensor film 4. For a multi-parameter analysis light sources of different wavelengths $\lambda_1$ and $\lambda_2$ (for example, $\lambda_1$=450 nm, $\lambda_2$=525 nm) may be used. For each light source 6, 8 or each array of light sources a suitable optical excitation filter 7, 9 may be positioned in the light path, if required. By means of the excitation filters undesirable radiation components of the excitation light are eliminated. The emission filter 12 in front of the focusing lens 11 is used to protect the detection unit 10 from backscattered or reflected excitation light, passing only the fluorescent light emitted by the sensor film 4. The focusing lens 11 may have a zoom function to vary the areal resolution of the images.

As compared to the traditional method of individual pointwise measurement of $O_2$ partial pressure by means of a miniature electrode, the system proposed by the invention is characterized by the following advantages:

Greater accuracy and reproducibility of the measuring process, as the fluorescent indicator of the sensor film will not consume oxygen but will only respond to local oxygen concentrations.

Independence of electromagnetic fields.

Possibility of determining the nutritive oxygen content of the skin to assist therapy-related decisions.

Short and painless measurements on the patient.

Physiologically harmless measuring temperatures (not more than 37° C).

Non-invasive measuring method.

Hygienic measuring method, as only the sensor film, which is discarded after measurement, is in direct contact with the patient's skin.

Detection and areally resolved presentation of the measured variable over a skin area of about 5×4 cm, by means of only one measuring process.

Suitable for two-dimensional measurements on curved surfaces.

Short duration of the measurement process (<5 sec).

Unambiguous mapping of the measured $O_2$ distribution onto the corresponding points of the skin.

Determining the distributions of measured values will permit the heterogeneity of measured values to be detected and utilized for statistical analysis.

A two-dimensional image is much more representative than individual point measurements.

Possibility of improved resolution by a change in imaging geometry.

Possibility of software-supported data evaluation and graphic representation on the monitor, where for certain measuring points (such as the cursor position) the measured value or its gradient may be displayed, also false color representation, minima-maxima, histograms, filing.

Simplicity of handling.

What is claimed is:

1. A system for quantitative determination of the local distribution of a quantity to be measured, comprising:

a planar sensor film applied to a measuring surface, said sensor film having known diffusion properties regarding a parameter to be determined, containing a luminescent indicator responding to said parameter to be determined with a change of at least one optical property;

an excitation and detection unit including means for supplying excitation radiation of at least one wavelength, an imaging detection means and an evaluation unit processing the image information obtained from said excitation and detection unit; and an applicator tube applied to said measuring surface, said applicator tube including a rim facing said measuring surface which includes an elastic supporting ring elastically contacting said sensor film, said applicator tube being impervious to external radiation interfering with said detection means.

2. A system as claimed in claim 1, wherein said planar sensor film applied to said measurement surface is a flexible sensing foil, a sensor paste or a spray layer.

3. A system as claimed in claim 1, wherein said sensor film on its side facing away from said measurement surface is provided with a barrier layer being impermeable to said parameter to be determined.

4. A system as claimed in claim 1, wherein said sensor film and additional supporting and filling layers consist of materials which exhibit a known, finite resistance to the passage of said parameter to be determined.

5. A system as claimed in claim 1, wherein said detection means comprise a unit for determining local fluorescence decay time of said luminescent indicator.

6. A system as claimed in claim 5, wherein said detection unit determines a quality which is derived from said local fluorescence decay time.

7. A system as claimed in claim 1, wherein a flexible layer is provided between said sensor film and said measurement surface bridging the gap between said sensor film and said measuring surface.

8. A system as claimed in claim 7, wherein said flexible layer is an adhesive layer which is permeable to said parameter to be determined.

9. A system as claimed in claim 7, wherein said flexible layer is impervious to radiation interfering with said detection unit.

10. A system as claimed in claim 1, wherein said applicator tube is provided at its coverable end facing away from said measuring surface with a coupling means for attaching the excitation and detection unit.

11. A system as claimed in claim 1, wherein said applicator tube is covered at its end facing away from said measurement surface by a cover being transparent to excitation and measurement radiation.

12. A system as claimed in claim 11, wherein said transparent cover is a glass plate.

13. A system as claimed in claim 1, wherein said applicator tube is covered at its end facing away from said measurement surface by a removable cap.

14. A system as claimed in claim 10, wherein said excitation and detection unit is attachable to said coupling means of said applicator tube so as to be rotatable about its optical axis.

15. A system as claimed in claim 1, wherein said applicator tube is provided with means for thermoregulation of said sensor film.

16. A system as claimed in claim 15, wherein said means for thermoregulation comprise inlet and outlet openings for a heat transfer medium.

17. A system as claimed in claim 1, wherein said applicator tube is provided with a radiation- or heating element for thermoregulation of said sensor film.

18. A system as claimed in claim 17, wherein said radiation element is an infrared light source.

19. A system as claimed in claim 17, wherein said heating element is an electric heater coil.

20. A system as claimed in claim 1, wherein said applicator tube is held in place at said measurement site by means of a cuff.

21. A system as claimed in claim 1, wherein a luminescent indicator is immobilized in said sensor film and the local luminescence quenching of said indicator is a unique function of the local oxygen concentration.

22. A system as claimed in claim 1, wherein said sensor film is coated with a luminescent indicator and the local luminescence quenching of said indicator is a unique function of the local oxygen concentration.

23. A system as claimed in claim 1, wherein said imaging detection means is a CCD camera.

* * * * *